United States Patent [19]

Ohwaki et al.

[11] Patent Number: 4,598,070
[45] Date of Patent: Jul. 1, 1986

[54] TRIPAMIDE AND CYCLODEXTRIN INCLUSION COMPOUND

[75] Inventors: Takayuki Ohwaki, Aichi; Shigeru Sakashita; Masahiro Kawahara, both of Gifu; Aishin Shinoda; Yasuo Miyake, both of Aichi, all of Japan

[73] Assignee: Eisai Co., Ltd., Tokyo, Japan

[21] Appl. No.: 631,997

[22] Filed: Jul. 18, 1984

[30] Foreign Application Priority Data

Jul. 21, 1983 [JP] Japan ................................ 58-131846

[51] Int. Cl.[4] ............................................. A61K 31/73
[52] U.S. Cl. ....................................... 514/58; 536/46; 536/103
[58] Field of Search .................. 424/180; 536/103, 46; 514/58

[56] References Cited

U.S. PATENT DOCUMENTS

| | | | |
|---|---|---|---|
| 4,228,160 | 10/1980 | Szejtli et al. | 424/180 |
| 4,407,795 | 10/1983 | Nicolau et al. | 424/180 |
| 4,424,209 | 1/1984 | Tuttle | 424/180 |
| 4,482,709 | 11/1984 | Iwao et al. | 424/180 |

OTHER PUBLICATIONS

The Merck Index, 1983, No. 9540.

Primary Examiner—Johnnie R. Brown
Assistant Examiner—Elli Peselev
Attorney, Agent, or Firm—Wenderoth, Lind & Ponack

[57] ABSTRACT

An inclusion compound composed of tripamide and cyclodextrin markedly improves the solubility of tripamide which is effective for treatment of essential hypertension.

3 Claims, 7 Drawing Figures

TRIPAMIDE AND CYCLODEXTRIN INCLUSION COMPOUND

BACKGROUND OF THE INVENTION

1. Field of the Invention

The present invention relates to an inclusion compound composed of tripamide and cyclodextrin.

2. Brief Description of the Prior Art

Tripamide which is to be included in accordance with the present invention is named N-(4-A2a-endo-tricyclo[5.2.1.0$^{2.6}$]decan-4-yl)-4-chloro-3-sulfamoyl-benzamide shown by structural formula:

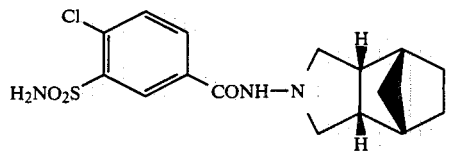

and commercially available as a curing agent of essential hypertension. However, this substance is soluble in water only with extreme difficulty. In actuality, it is understood that the solubility of the substance in water, the solubility in the Liquid I used for the disintegration test of the Japanese Pharmacopoeia (hereinafter referred to "Liquid I of the Japanese Pharmacopoeia") and the solubility in the Liquid II used for the disintegration test of the Japanese Pharmacopoeia (hereinafter referred to "Liquid II of the Japanese Pharmacopoeia") is low, as is seen from the sample for comparison in Example 2 later described. Liquid I of the Japanese Pharmacopoeia is prepared by adding, to 2.0 g of sodium chloride, 6.0 ml of a diluted hydrochloric acid and water, so as to make the total volume to 1000 ml. The Liquid I is colorless and transparent, and its pH is about 1.2. Liquid II of the Japanese Pharmacopoeia is prepared by adding, to 35.8 g of sodium monohydrogenphosphate, 6.0 ml of a diluted hydrochloric acid and water, thereby making the total volume to 1000 ml. The Liquid II is colorless and transparent, and its pH is about 7.5.

Techniques for improving solubility of pharmaceuticals using cyclodextrin are already widely known in the art. For example, upon improvement of the solubility of pharmaceutical compounds such as barbituric acid derivatives, mefenamic acid, indomethacine, chloramphenicol, etc., it is known that cyclodextrin exhibits its best usefulness. However, the usefulness is not obviously applicable to general pharmaceuticals, but has been developed only by discovering respective applications corresponding to respective pharmaceuticals. In attempting to apply to tripamide, techniques specific to tripamide have been taken into account and by confirming the formation of an inclusion compound and the improved solubility thereby, the present invention has been perfected.

Under the foregoing circumstances, the present inventors have extensively investigated methods of improving the solubility of tripamide and as a result, have found that the aimed object has been achieved by converting the substance into an inclusion compound using cyclodextrin as a host and, have accomplished the present invention.

SUMMARY OF THE INVENTION

An object of the present invention is to provide an inclusion compound composed of tripamide and cyclodextrin which provides improved solubility in an aqueous medium.

DETAILED DESCRIPTION OF THE PREFERRED EMBODIMENTS

Figure 1:
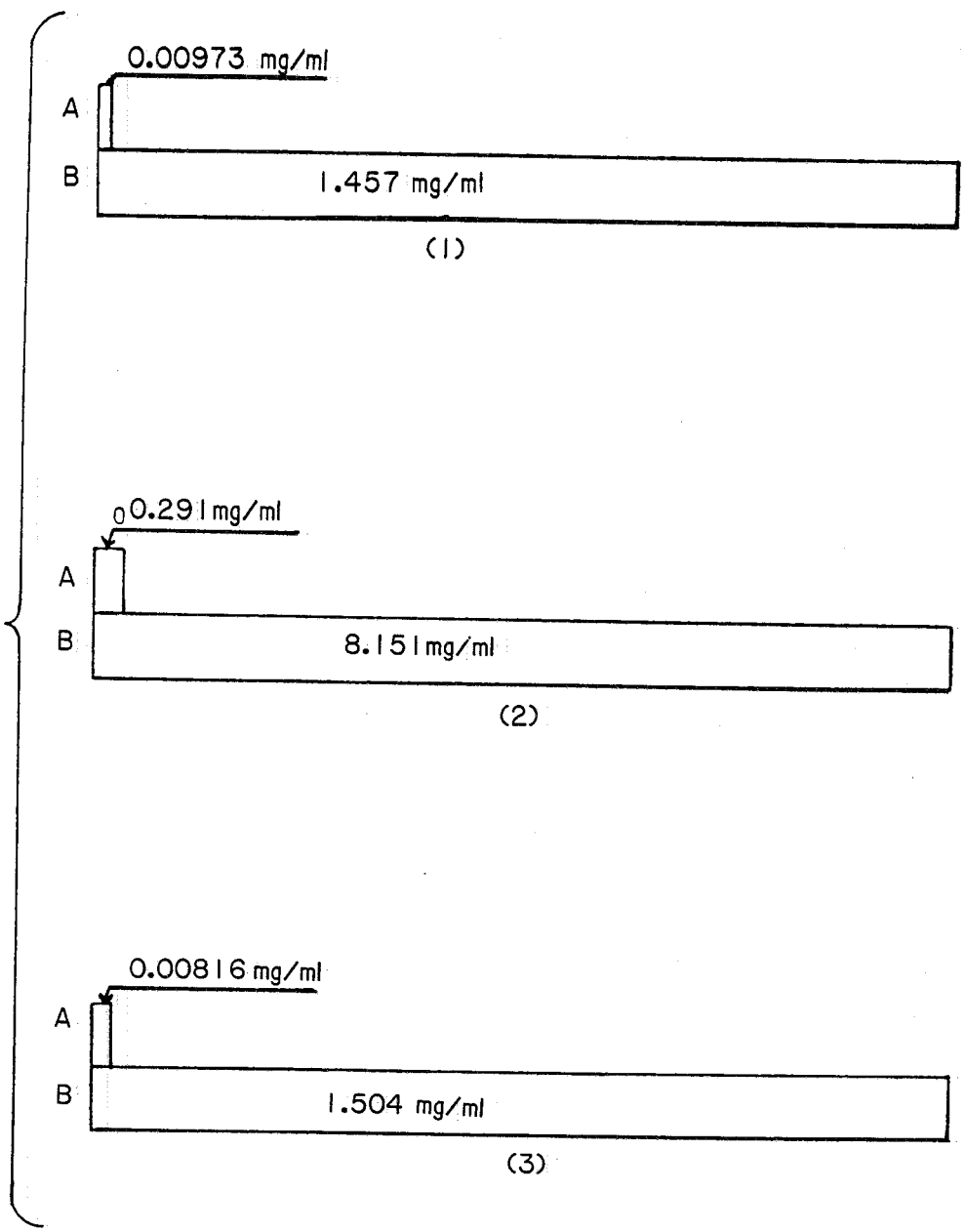
FIG. 1 corresponds to FIG. 1 in Experiment 1, entitled "Results", indicating the measurement results of the solubility of tripamide.

The inclusion compound of the present invention is composed of tripamide and cyclodextrin. Herein cyclodextrin may be any kind but particularly preferred are β-cyclodextrin and γ-cyclodextrin.

To distinguish the inclusion compound of the present invention over tripamide per se or a mere mixture of tripamide and cyclodextrin is made possible by the analysis of the solubility phase diagram, differential thermal analysis (DSC) and, the results of the powder X ray diffraction and the infrared absorption spectrum analysis, as shown in the examples later described. That is, in the solubility phase diagram in which the addition amount of cyclodextrin is plotted on the axis of abscissas and the total solubility of tripamide on the axis of ordinates, it is observed that as the addition amount of cyclodextrin as a host molecule increases, the total solubility of tripamide increases, from which it is understood that an interaction obviously exists between tripamide and cyclodextrin. In addition, tripamide per se exhibits a marked melting phenomenon at about 255° C. Accordingly, tripamide shows a clear endothermic pattern in DSC but the inclusion compound of the present invention does not require any absorption of heat and does not exhibit the corresponding endothermic pattern, since each molecule of tripamide is already fixed in the inclusion compound. Furthermore, when a comparison in the powder X ray diffractions is made between crystals of tripamide per se, crystals of cyclodextrin as the host molecule of the inclusion compound or a mere mixture of tripamide and cyclodextrin and the inclusion compound of the present invention, the crystalline structure of the inclusion compound of the present invention is obviously different from any one of the crystal structures of tripamide per se, and cyclodextrin used as the host molecule of the inclusion compound. Further, tripamide per se possesses characteristic absorption peaks at 1550 cm$^{-1}$ and 1650 cm$^{-1}$ in the infrared absorption spectrum but the inclusion compound of the present invention shows a disappearance of the characteristic absorption peak at 1550 cm$^{-1}$ and contraction of the characteristic absorption peak at 1650 cm$^{-1}$. This is assumed to be because of the vibration of the secondary amide at 1550 cm$^{-1}$ and the vibration of carbonyl at 1650 cm$^{-1}$ in the amide bond moiety of the chlorobenzosulfonamide nucleus and the endo-methyleneperhydroisoindoline nucleus of tripamide itself would be inhibited due to the formation of the inclusion compound.

Also with the mere mixture of tripamide and cyclodextrin, the results on DSC, the powder X ray diffraction and the infrared absorption spectrum are the same as those obtained with tripamide per se. Therefore, such a mere mixture is distinguishable from the inclusion compound of the present invention similarly by DSC, the powder X ray diffraction and the infrared absorption spectrum.

To prepare the inclusion compound of the present invention, a conventionally known process is applicable. Accordingly, for example, cyclodextrin may be dissolved in Liquid I of the Japanese Pharmacopeia and tripamide is mixed with the resulting solution. Stirring is conducted at 40° C. for 1 to 2 days. The reaction mixture is cooled in ice water. The formed precipitates are taken out by filtration and dried. In this case, it is appropriate that at least 0.5 mole, preferably 2 to 3 moles, of cyclodextrin be added to 1 mole of tripamide.

The inclusion compound of the present invention is useful for improving the solubility of tripamide. As will be shown in the examples later described, when tripamide is dissolved in water, Liquid I of the Japanese Pharmacopeia or Liquid II of the Japanese Pharmacopeia, it is observed that the solubility of tripamide is improved.

The effects of the present invention will be explained with reference to the experiments below.

EXPERIMENT 1

Sample

The inclusion compound prepared in accordance with the process described in Example 1 was used as a sample. This sample was prepared by the reaction of 1 mole of tripamide and 3 moles of β-cyclodextrin. For purpose of comparison, tripamide per se was used.

Method

The sample was accurately weighed 100 mg as tripamide and mixed with water, Liquid I of the Japanese Pharmacopeia or Liquid II of the Japanese Pharmacopeia. The mixture was stirred at 37° C. in a warm bath for 5 days. Tripamide, dissolved in the solution, was measured by the absorbancy method.

That is, each of the tripamide solutions in water, Liquid I of the Japanese Pharmacopeia and Liquid II of the Japanese Pharmacopeia was filtered using a millipore filter of 1.2 μm and 1 ml each of the solutions after filtration was taken out. In the case of the solution using Liquid I of the Japanese Pharmacopeia, the solution was further diluted with Liquid I of the Japanese Pharmacopeia to make a 100 ml solution and 5 ml taken out of the resulting solution was further diluted to 50 ml with a 0.1N hydrochloric acid-methanol solution followed by measurement at 244 nm. In the case of each of the solutions in water and Liquid II of the Japanese Pharmacopeia, the solution was diluted to 100 ml with Liquid II of the Japanese Pharmacopeia followed by measurement at 233 nm.

Results

The results are shown in FIG. 1, wherein (1) indicates the results of the measurement of the solubility in water, (2) indicates results of the measurement of the solubility in Liquid I of the Japanese Pharmacopeia and (3) indicates the results of the measurement of the solubility in Liquid II of the Japanese Pharmacopeia; and A represents the solubility of tripamide per se and B presents the solubility when it was made into the inclusion compound.

From FIG. 1, it is understood that the inclusion compound of the present invention improves the solubility of tripamide.

EXPERIMENT 2

Sample and Method

Three (3) kinds of the inclusion compounds in which 1 mole, 2 moles and 3 moles of β-cyclodextrin were employed per 1 mole of tripamide in the preparation were prepared in a manner similar to Example 1.

With each of the samples, experiments were performed in accordance with the method described in "Method" of Experiment 1.

Results

The results are shown in Table 1. From Table 1, it is understood that the inclusion compounds of the present invention improve the solubility of tripamide. It is further understood that as the addition amount of β-cyclodextrin increases, the solubility of tripamide increases.

TABLE 1

| Sample | Solubility (mg/ml) Solution | | |
| --- | --- | --- | --- |
| | Water | Japanese Pharmacopeia Liquid I | Japanese Pharmacopeia Liquid II |
| Tripamide | 0.0094 | 0.3491 | 0.0144 |
| Inclusion | | | |
| Compound: | | | |
| 1 | 0.1175 | 3.8269 | 0.2009 |
| 2 | 0.3995 | 6.8586 | 0.3955 |
| 3 | 0.5640 | 7.5047 | 0.5839 |

EXPERIMENT 3

Sample and Method

The inclusion compound was prepared in a manner similar to Example 1 except that cyclodextrin was γ-cyclodextrin and 3 moles of γ-cyclodextrin were used per 1 mole of tripamide. The inclusion compound was used as a sample.

With the sample, experiments were performed in accordance with "Method" of Experiment 1.

Results

Figure 2:
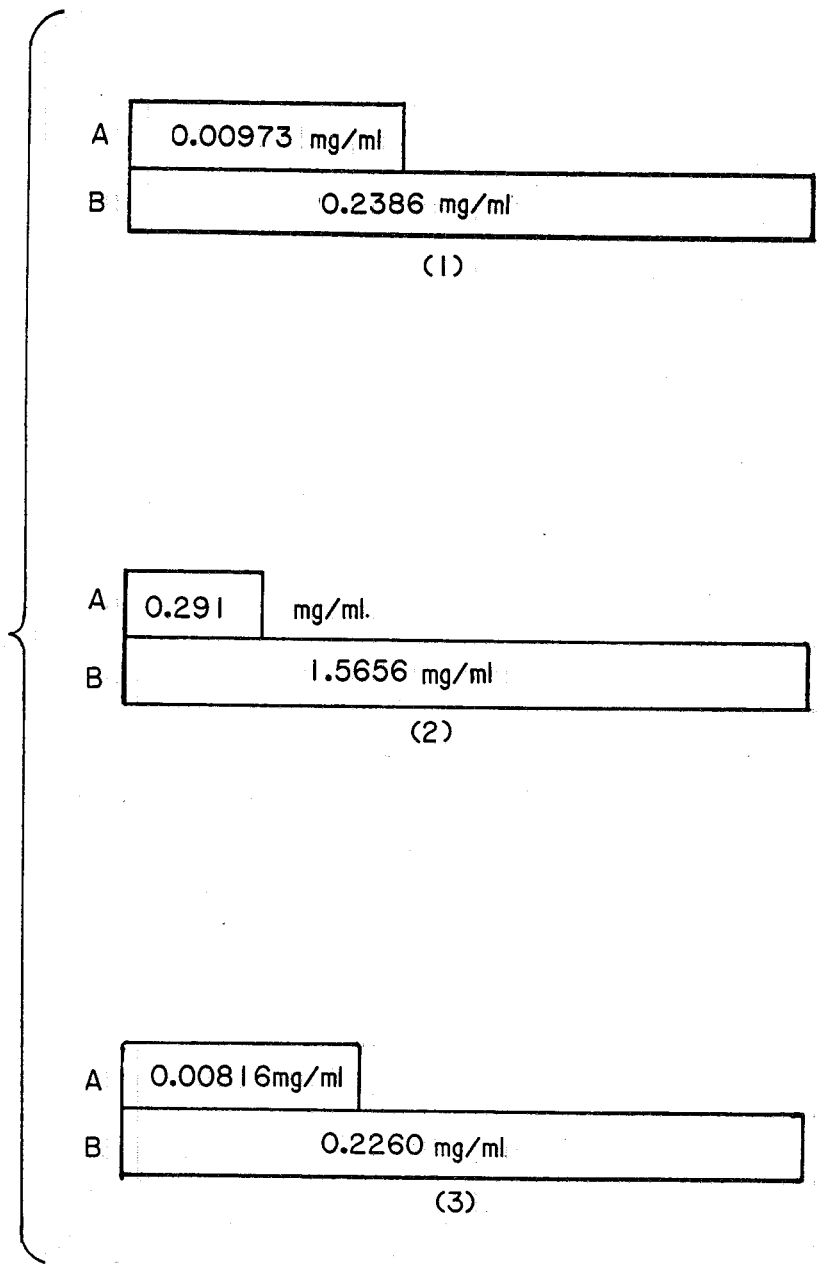
FIG. 2 corresponds to FIG. 2 in Experiment 3, entitled "Results", indicating the measurement results of the solubility of tripamide.

The results are shown in FIG. 2, wherein (1) indicates the results of the measurements of the solubility in water, (2) indicates the results of the measurement of the solubility in Liquid I of the Japanese Pharmacopeia and (3) indicates the results of the measurements of the solubility in Liquid II of the Japanese Pharmacopeia; and A represents the solubility of tripamide per se and B presents the solubility when it was made an inclusion compound.

From FIG. 2, it is understood that the inclusion compound of the present invention improves the solubility of tripamide.

The present invention will be described in more detail with reference to the following examples.

EXAMPLE 1

Tripamide, 4 g, was accurately weighed. Separately, 36.82 g of β-cyclodextrin was dissolved in 1000 ml of Liquid I of the Japanese Pharmacopeia. Both were mixed and the mixture was stirred at 40° C. for 48 hours on a warm bath. The solution mixture was filtered and the filtrate was cooled in ice water. The formed precipitates were taken out by filtration. After washing the precipitates with water and acetone, they were dried under reduced pressure. The molar ratio of β-cyclodextrin used in this preparation was 3 moles per 1 mole of tripamide.

With the thus obtained precipitation product, DSC, powder X ray diffraction and infrared absorption spectrum analysis were conducted under the following conditions.

DSC: temperature elevation speed 10° C./min., Range±4 m cal

Powdery X ray diffraction:
Target Cu/Monochrometer
Detector SC

Infrared absorption spectrum: KBr method

For purpose of comparison, tripamide per se and a mere mixture of tripamide and β-cyclodextrin in which the contents of both components were the same as the precipitation product were prepared and DSC, powder X ray diffraction and infrared absorption spectrum analysis were likewise performed therewith.

Figure 3:
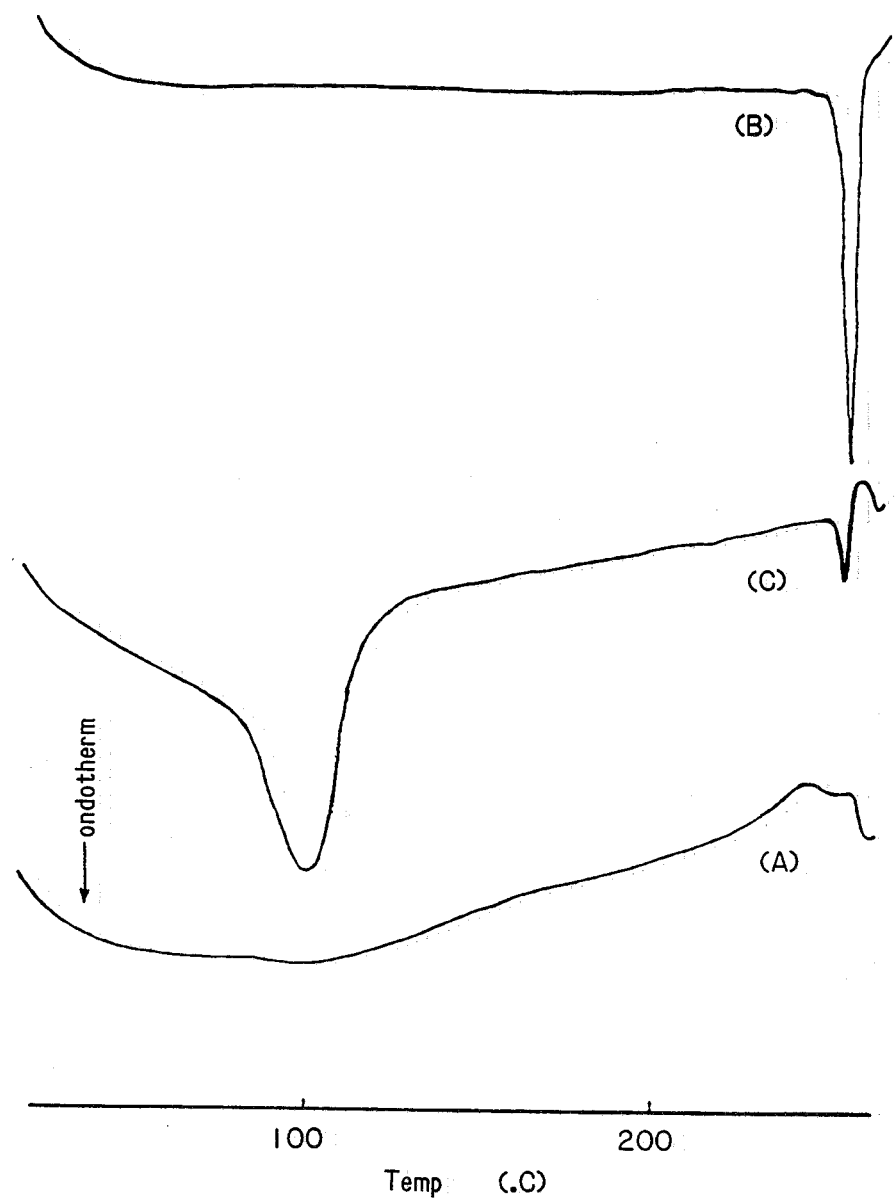
FIG. 3 corresponds to FIG. 3 in Example 1, indicating the results of differential thermal analysis (DSC).

The results are shown in FIGS. 3 through 7. FIG. 3 shows the results of DSC wherein the lines represented by symbols A, B and C indicate the results of DSC with respect to the precipitation product obtained in this example, tripamide per se and a mere mixture of tripamide and β-cyclodextrin wherein the contents of both components were the same as the precipitation product, respectively.

Figure 4:
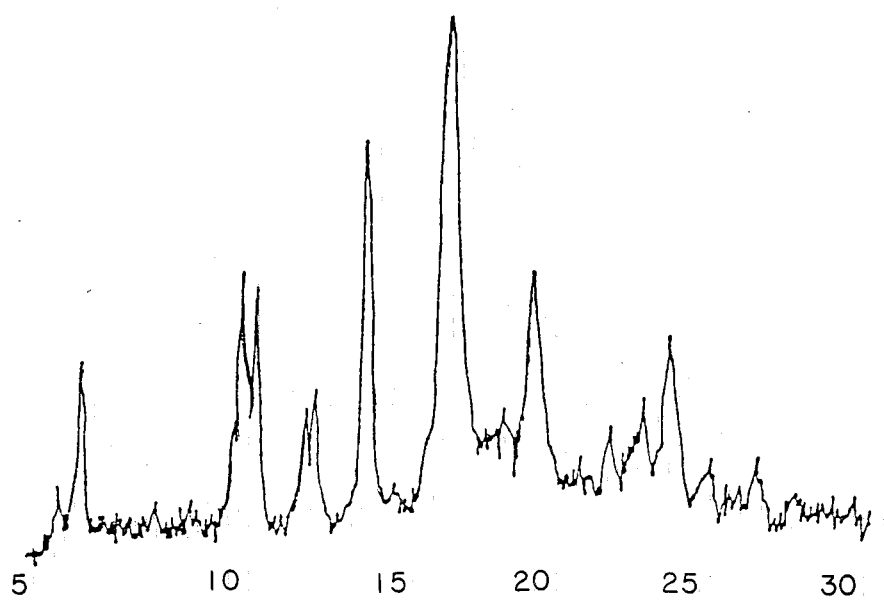
FIGS. 4, 5 and 6 correspond to FIGS. 4, 5 and 6 described in Example 1, respectively, showing a graph on the precipitated product in FIG. 4, a graph on tripamide per se in FIG. 5 and a graph on the powder X ray diffraction pattern of the mixture in FIG. 6.
Figure 5:
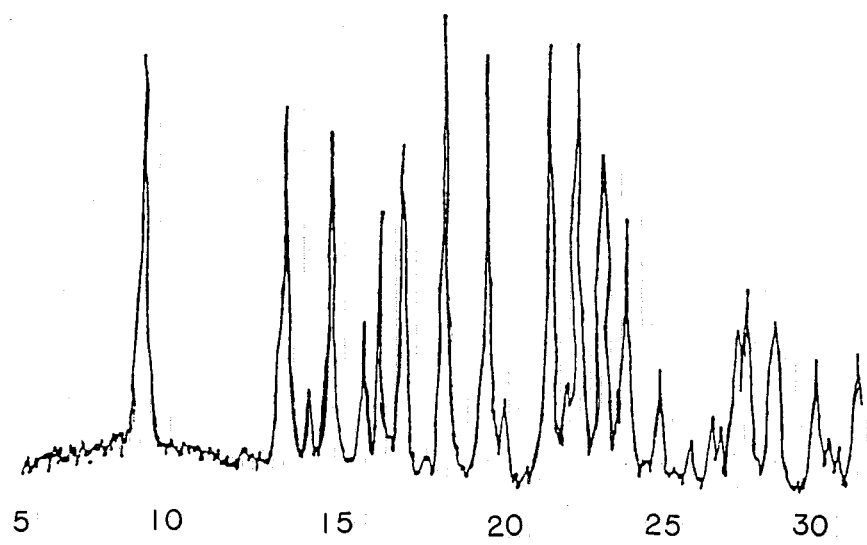
Figure 6:
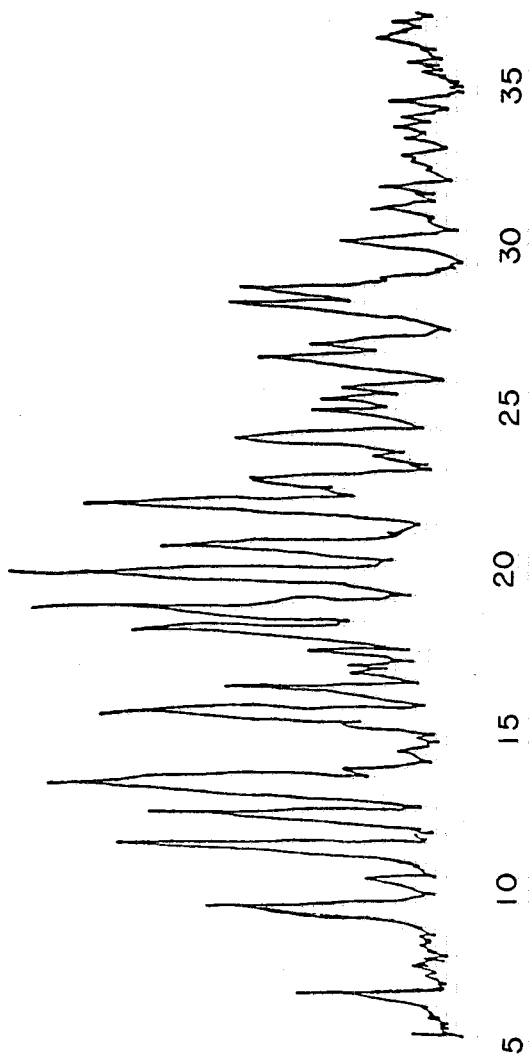

FIGS. 4, 5 and 6 show the powder X ray diffractions with respect to the precipitated product obtained in this example, tripamide perse, and a mere mixture of tripamide and β-cyclodextrin wherein the contents of both components were the same as the precipitation product, respectively.

Figure 7:
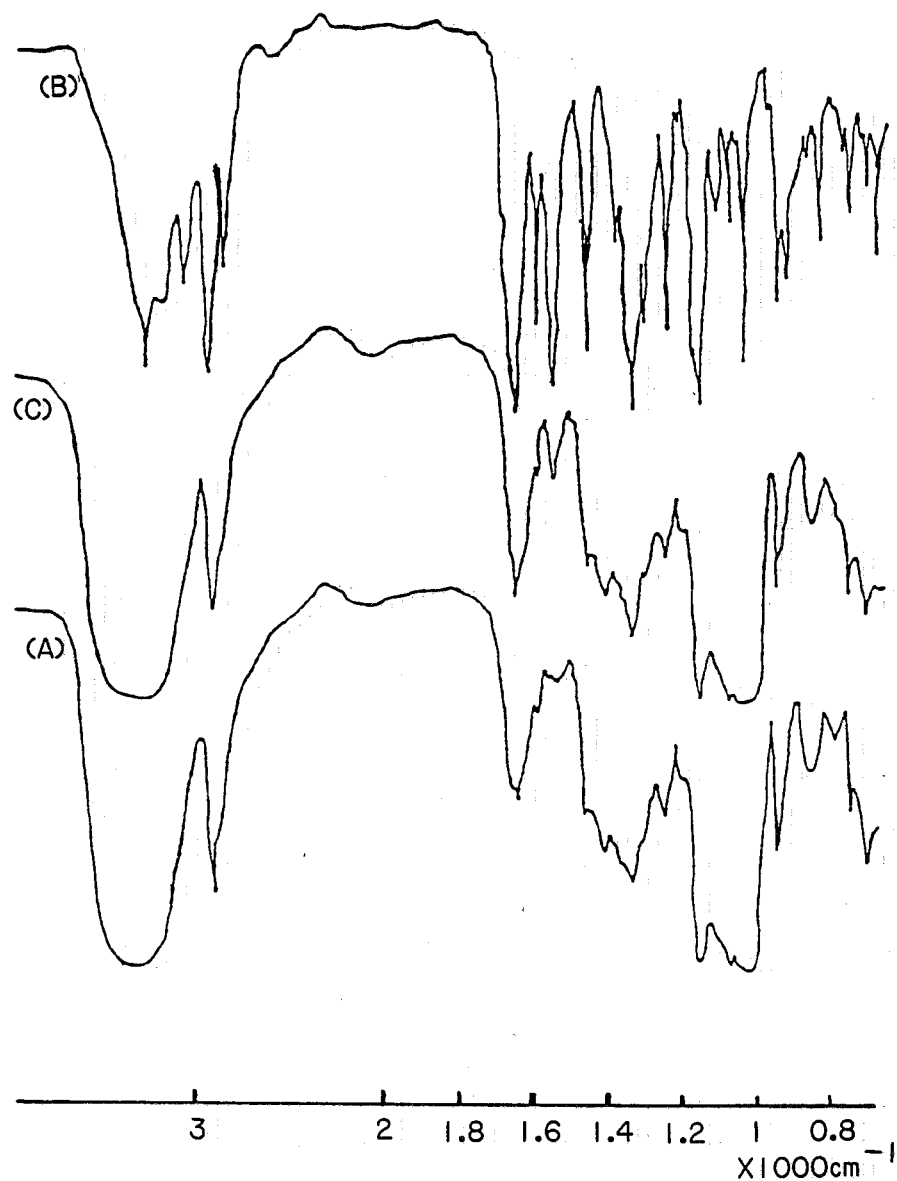
FIG. 7 corresponds to FIG. 7 described in Example 1 and is a graph showing the results of infrared absorption spectrum analysis.

FIG. 7 shows a graph indicating the results of the infrared absorption spectrum analysis wherein the lines represented by symbols A, B and C indicate the results on infrared absorption spectra with respect to the precipitated product obtained in this example, tripamide per se, and a mere mixture of tripamide and β-cyclodextrin wherein the contents of both components were the same as the precipitation product, respectively.

From FIGS. 3 through 7, it is understood that crystallization inherent to the tripamide molecule is inhibited by the intervention of β-cyclodextrin in the precipitation product obtained in this example. It is therefore understood that the precipitation product is an inclusion compound composed of tripamide and β-cyclodextrin.

EXAMPLE 2

An inclusion compound composed of tripamide and α-cyclodextrin was prepared in a manner similar to Example 1 except that α-cyclodextrin was used in place of β-cyclodextrin.

EXAMPLE 3

An inclusion compound composed of tripamide and γ-cyclodextrin was prepared in a manner similar to Example 1 except that γ-cyclodextrin was used in place of β-cyclodextrin.

While the invention has been described in detail and with reference to specific embodiments thereof, it will be apparent from one skilled in the art that various changes and modifications can be made therein without departing from the spirit and scope thereof.

What is claimed is:

1. An inclusion compound composed of tripamide represented by formula:

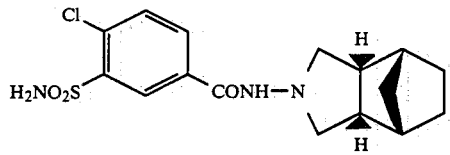

and from 1.0 to 3 moles cyclodextrin per mole of tripamide.

2. The inclusion compound as claimed in claim 1 wherein the cyclodextrin is α-cyclodextrin, β-cyclodextrin or γ-cyclodextrin.

3. An inclusion compound according to claim 1 in which the cyclodextrin is present in an amount of 2 to 3 moles per mole of tripamide.